(12) United States Patent
Smedt et al.

(10) Patent No.: US 7,193,715 B2
(45) Date of Patent: Mar. 20, 2007

(54) MEASUREMENT OF OVERLAY USING DIFFRACTION GRATINGS WHEN OVERLAY EXCEEDS THE GRATING PERIOD

(75) Inventors: Rodney Smedt, Los Gatos, CA (US); Abdurrahman Sezginer, Los Gatos, CA (US); Hsu-Ting Huang, Sunnyvale, CA (US)

(73) Assignee: Tokyo Electron Limited, Tokyo (JP)

( * ) Notice: Subject to any disclaimer, the term of this patent is extended or adjusted under 35 U.S.C. 154(b) by 432 days.

(21) Appl. No.: 10/714,460

(22) Filed: Nov. 14, 2003

(65) Prior Publication Data

US 2004/0137651 A1    Jul. 15, 2004

Related U.S. Application Data

(60) Provisional application No. 60/426,156, filed on Nov. 14, 2002.

(51) Int. Cl.
| | |
|---|---|
| *G01B 11/00* | (2006.01) |
| *G03F 9/00* | (2006.01) |
| *G03C 5/00* | (2006.01) |
| *H01L 23/544* | (2006.01) |
| *H01L 21/76* | (2006.01) |

(52) U.S. Cl. ................ 356/401; 257/797; 430/22; 430/30; 438/401

(58) Field of Classification Search ............ None
See application file for complete search history.

(56) References Cited

U.S. PATENT DOCUMENTS

| | | | |
|---|---|---|---|
| 4,200,395 A | 4/1980 | Smith et al. ............. 356/356 |
| 4,757,207 A | 7/1988 | Chappelow et al. ..... 250/491.1 |
| 5,216,257 A | 6/1993 | Brueck et al. ........... 250/548 |
| 5,343,292 A | 8/1994 | Brueck et al. ........... 356/363 |
| 5,805,290 A | 9/1998 | Ausschnitt et al. ....... 356/401 |
| 6,023,338 A | 2/2000 | Bareket .................... 356/401 |
| 6,079,256 A | 6/2000 | Bareket .................... 73/105 |
| 6,462,818 B1 | 10/2002 | Bareket .................... 356/401 |
| 6,483,580 B1 | 11/2002 | Xu et al. .................. 356/300 |
| 6,772,084 B2 * | 8/2004 | Bischoff et al. ......... 702/127 |
| 6,842,220 B1 * | 1/2005 | Dishon et al. ............ 355/27 |
| 2002/0149782 A1 * | 10/2002 | Raymond ................ 356/616 |
| 2002/0158193 A1 | 10/2002 | Sezginer et al. ......... 250/237 |

(Continued)

FOREIGN PATENT DOCUMENTS

WO    WO 02/25723 A2    3/2002

(Continued)

OTHER PUBLICATIONS

H-T. Huang et al., "Scatterometry-Based Overlay Metrology," *Metrology, Inspection, and Process Control for Microlithography XVII, Proceedings of SPIE*, vol. 5038 (2003), pp. 126-137.

(Continued)

*Primary Examiner*—Gregory J. Toatley, Jr.
*Assistant Examiner*—Gordon J. Stock, Jr.
(74) *Attorney, Agent, or Firm*—Stallman & Pollock LLP

(57) ABSTRACT

A method for measuring overlay in semiconductor wafers includes obtaining diffraction based and imaging based measurements of the same target. The two separate measurements are then combined in a way that is consistent to both measurements to obtain an overlay measurement that has high precision and large range.

22 Claims, 6 Drawing Sheets

U.S. PATENT DOCUMENTS

| | | | |
|---|---|---|---|
| 2002/0192577 A1 | 12/2002 | Fay et al. | 430/22 |
| 2003/0002043 A1 | 1/2003 | Abdulhalim et al. | 356/400 |
| 2003/0042579 A1 | 3/2003 | Schulz | 257/629 |
| 2003/0043372 A1 | 3/2003 | Schulz | 356/327 |
| 2003/0044702 A1 | 3/2003 | Schulz | 430/30 |
| 2003/0190793 A1 | 10/2003 | Brill et al. | 438/401 |
| 2006/0065625 A1* | 3/2006 | Abdulhalim et al. | 216/59 |

FOREIGN PATENT DOCUMENTS

| | | | |
|---|---|---|---|
| WO | WO 2065545 A2 * | 8/2002 | |

OTHER PUBLICATIONS

P. Heimann, "The Color-Box alignment vernier: a sensitive lithographic alignment vernier read at low magnification," *Optical Engineering*, vol. 29, No. 7, Jul. 1990, pp. 828-836.

K.M. Monahan, "Handbook of Critical Dimension Metrology and Process Control," *Critical Reviews of Optical Science and Technology, SPIE*, vol. CR52, proceedings of a conference held Sep. 28-29, 1993, pp. cover, 160-188.

* cited by examiner

Offset ξ

MEASUREMENT OF OVERLAY USING DIFFRACTION GRATINGS WHEN OVERLAY EXCEEDS THE GRATING PERIOD

PRIORITY CLAIM

The present application claims priority to U.S. Provisional Patent Application Ser. No. 60/426,156, filed Nov. 14, 2002, which is incorporated in this document by reference.

TECHNICAL FIELD

This invention relates to measuring the pattern overlay alignment accuracy of a pair of patterned layers on a semiconductor wafer, possibly separated by one or more layers, made by two or more lithography steps during the manufacture of semiconductor devices.

BACKGROUND OF THE INVENTION

Manufacturing semiconductor devices involves depositing and patterning several overlaying layers. A typical semiconductor wafer might include, for example, a series of gates formed on a first layer and a series of interconnects formed on a second layer. The two layers (and their structures) are formed at different lithography steps in the manufacturing process. Alignment between the two layers is critical to ensure proper connection between the gates and their interconnects. Typically, this means that the tolerance of alignment must be less than the width of a single gate.

Overlay is defined as the displacement of a patterned layer from its ideal position aligned to a layer patterned earlier on the same wafer. Overlay is a two dimensional vector ($\Delta x$, $\Delta y$) in the plane of the wafer. Overlay is a vector field, i.e., the value of the vector depends on the position on the wafer. Perfect overlay and zero-overlay are used synonymously. Overlay and overlay error are used synonymously. Depending on the context, overlay may signify a vector or one of the components of the vector.

Overlay metrology provides the information that is necessary to correct the alignment of the stepper-scanner and thereby minimize overlay error with respect to previously patterned layers. Overlay errors, detected on a wafer after exposing and developing the photoresist, can be corrected by removing the photoresist, repeating exposure on a corrected stepper-scanner, and repeating the development of the photoresist. If the measured error is acceptable but measurable, parameters of the lithography process could be adjusted based on the overlay metrology to avoid excursions for subsequent wafers.

Most prior overlay metrology methods use built-in test patterns etched or otherwise formed into or on the various layers during the same plurality of lithography steps that form the patterns for circuit elements on the wafer. One typical pattern, called "box-in-box" consists of two concentric squares, formed on a lower and an upper layer, respectively. "Bar-in-bar" is a similar pattern with just the edges of the "boxes" demarcated, and broken into disjoint line segments. The outer bars are associated with one layer and the inner bars with another. Typically one is the upper pattern and the other is the lower pattern, e.g., outer bars on a lower layer, and inner bars on the top. However, with advanced processes the topographies are complex and not truly planar so the designations "upper" and "lower" are ambiguous. Typically they correspond to earlier and later in the process. The squares or bars are formed by lithographic and other processes used to make planar structures, e.g., chemical-mechanical planarization (CMP).

In one form of the prior art, a high performance microscope imaging system combined with image processing software estimates overlay error for the two layers. The image processing software uses the intensity of light at a multitude of pixels. Obtaining the overlay error accurately requires a high quality imaging system and means of focusing the system. One requirement for the optical system is very stable positioning of the optical system with respect to the sample. Relative vibrations blur the image and degrade the performance. Reducing vibration is a difficult requirement to meet for overlay metrology systems that are integrated into a process tool, like a lithography track.

As disclosed in U.S. Patent Application Serial No. 2002/0158193; U.S. Patent Application No. 2003/0190793 A1; and as described in Proc. of SPIE Vol. 5038 February 2003 "Scatterometry-Based Overlay Metrology" by Huang et al., p. 126–137 and "A novel diffraction based spectroscopic method for overlay metrology" by Yang et al. p. 200–207 (all four incorporated in this document by reference) one approach to overcome these difficulties is to use overlay metrology targets that are made of a stack of two diffraction gratings as shown in FIG. 1. The grating stack 10 has one grating 20 in the lower layer and another grating 30 in the upper layer as shown in FIG. 1. The layers of 20 and 30 are to be aligned. There are two instances of the grating stack 10, one for the x-component of overlay and one for the y-component. The measurement instrument is such that it does not resolve individual grating lines. It measures overall optical properties of the entire grating. Optical properties are measured as a function of wavelength, polar or azimuthal angle of incidence, polarization states of the illumination and the detected light, or any combination of these independent variables. An alternative embodiment uses two stacks of line gratings to measure x-overlay and two stacks of line gratings to measure y-overlay (four grating stacks total). Still another embodiment uses three line grating stacks in combination to simultaneously measure both x and y alignment. (See also PCT publication WO 02/25723A2, incorporated herein by reference). Scatterometry (diffraction) is proving to be an effective tool for measuring overlay.

A shortcoming of the prior scatterometry-based art is that, diffraction gratings cannot distinguish overlay values that differ by an integer number of periods. Let $R(\lambda,\theta,\xi)$ denote the specular (0-th order) reflection of the grating at wavelength $\lambda$, angle of incidence $\theta$, and offset $\xi$. The offset $\xi$ is the distance between centerlines of lower and upper grating lines as shown in FIG. 1. The function $R(\lambda,\theta,\xi)$ is periodic with respect to the offset $\xi$:

$$R(\lambda,\theta,\xi)=R(\lambda,\theta,\xi+P) \qquad (1)$$

where P is the period of the grating. The scatterometry-based overlay measurements are even more ambiguous when the profiles of the grating lines are symmetric. Then, a consequence of reciprocity is:

$$R(\lambda,\theta,\xi)=R(\lambda,\theta,-\xi) \qquad (2)$$

$$R(\lambda,\theta,(P/2)+\xi)=R(\lambda,\theta,(P/2)-\xi) \qquad (3)$$

There are two values of offset, separated by P/2, where the optical properties become ambiguous. Optical properties are insensitive to overlay at these points. Therefore, the largest measurement range is P/2 when the grating lines have symmetric cross-sections. If the unit cell of the grating is substantially asymmetric, the measurement range becomes P, a whole period. Huang et al., cited above, describe means of manufacturing a grating with an asymmetric unit cell. The measurement range also becomes a whole period if two grating stacks are used, the offset of each stack is biased, and the two offset biases differ by P/4 (as described in U.S. application Ser. No. 10/613,378, filed Jul. 3, 2003, incorporated in this document by reference).

FIG. 2 shows the calculated near-normal incidence, unpolarized reflectance of a grating stack as a function of offset ξ. Each curve corresponds to a different wavelength. The ambiguity described by Equations (2) and (3) is clearly visible in FIG. 2. The ordinate of the graph in FIG. 3 shows overlay measured using diffraction gratings with a 1 μm period and 1:1 line to space ratio. Overlay was obtained by fitting the reflection spectra of a pair of gratings with rigorous coupled wave analysis. The abscissa shows the best estimate of the actual value of overlay, which is the sum of the overlay that was intentionally written to the reticle that produced the gratings and the overlay that was imparted by the lithography stepper-scanner. Overlay measured using gratings is not valid when it approaches or exceeds ±P/4 (250 nm in this example). FIG. 4 is an abstraction that shows the periodic nature of the overlay measured using diffraction gratings. The overlay measured by the grating, $\Delta x_{GRATING}$, is related to the actual overlay as follows:

$$N = int\left[\frac{\Delta x_{ACTUAL}}{P/2}\right] \quad (4)$$

$$\Delta x_{GRATING} = (-1)^N [\Delta x_{ACTUAL} - N\,P/2]$$

In Equation (4), int[x] denotes the integer nearest to x. In prior art, the integer N is unknown. Therefore, $\Delta x_{GRATING}$ represents $\Delta x_{ACTUAL}$ only when N is zero, that is, when $|\Delta x_{ACTUAL}| < P/4$. $\Delta x_{GRATING}$, which is also called fine-overlay measurement, has high precision but it is only accurate when N=0. Gross overlay is defined as the condition $|\Delta x_{ACTUAL}| \geq P/4$ or $|\Delta y_{ACTUAL}| \geq P/4$, that is, any one component of overlay exceeding a quarter of the period. Gratings cannot detect gross overlay until overlay gets so large that the upper and lower gratings do not overlap in part of the measurement spot. Although gross overlay is rare in well-tuned lithography processes, alignment errors larger than 100 nm, even as large as several microns occur when a new process, a new reticle, or a new projector is introduced. In these instances, there is a need to not only detect but also to measure gross overlay.

Although increasing the period increases the measurement range, P/2, this approach is not preferred because it reduces the sensitivity of the optical response of grating stacks to overlay. As the period is increased, if the period becomes a significant fraction of the diameter of the measurement spot, the placement of the spot on the grating affects the overlay measurement and reduces its precision. For these two reasons, increasing the period to increase the measurement range is counter-productive. Using more than one grating stack, each with a different period, reduces but does not eliminate ambiguity.

SUMMARY

An embodiment of the present invention provides a method and apparatus for measuring overlay. For a typical implementation, one or more grating stacks are included in a semiconductor wafer. Each grating stack includes an upper grating and a lower grating, each formed on one of the two layers for which overlay is to be measured. Each grating typically has a square or rectangular shape in the X-Y plane defined by the surface of the semiconductor wafer. At least one of the gratings stacks is configured so that its upper grating is larger or smaller (in the X or Y direction) than its lower grating.

For the method of the present invention, gross overlay is first measured by analyzing one or more grating stacks. Each gross overlay measurement is obtained by measuring, using optical microscopy, a grating stack that includes upper and lower gratings of different size. A fine (i.e., non-gross) overlay measurement is then obtained by scatterometry. Typically, this means that a probe beam is directed at one or more of the grating stacks and the resulting diffraction is analyzed to determine the fine overlay between the upper and lower layers being analyzed.

The gross and fine overlay measurements are then combined in a way that is consistent with each measurement. Typically, this means that the gross overlay measurement is normalized to locate a starting point for the fine overlay measurement. The fine overlay measurement is then added or subtracted to that starting point to define a total overlay measurement.

DETAILED DESCRIPTION OF THE PREFERRED EMBODIMENTS

Figure 5:
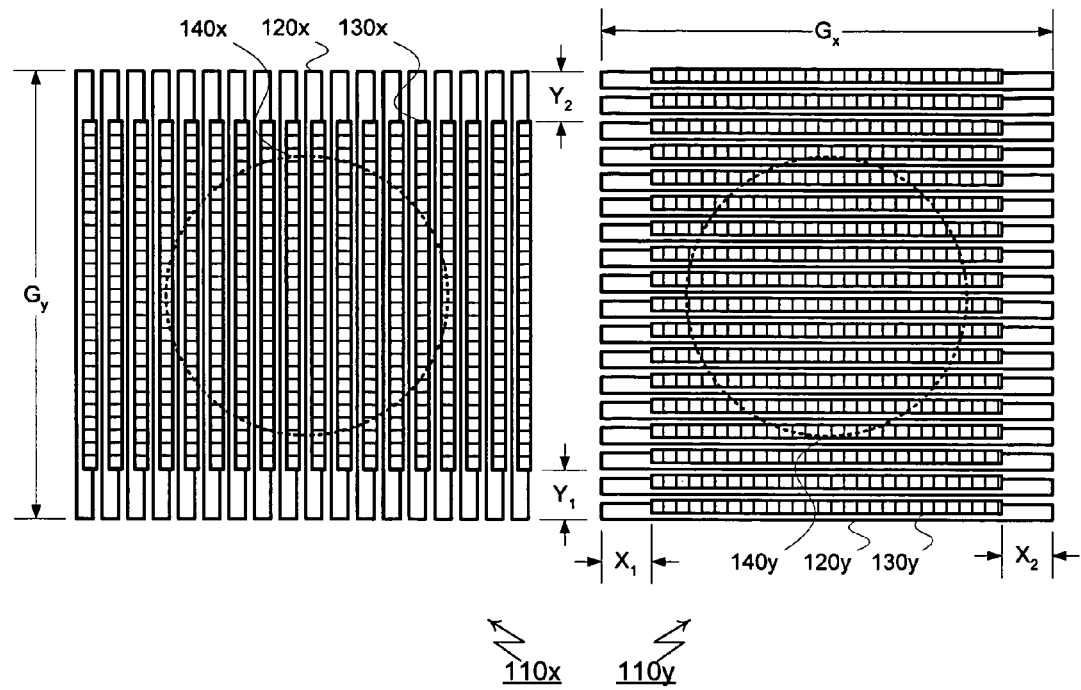
FIG. 5 shows overlay metrology target according to an embodiment of the present invention.
Figure 6:
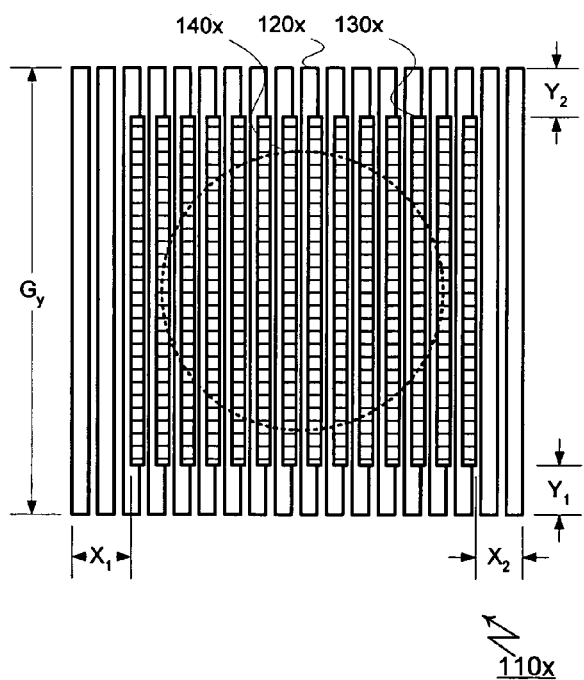
FIG. 6 shows another embodiment for the overlay metrology target configured, in this case to measure overlay in two directions using a single grating stack.

Referring to FIG. 5, overlay target 110 contains at least one grating stack 110x that measures the x-component of the overlay and at least one grating stack 110y that measures the y-component of the overlay. The grating stack 110x and 110y are, for example, placed in the scribe lines, or alleys, between dies on a semiconductor wafer. Grating stack 110x and 110y are measured preferably one at a time (sequentially) by an optical instrument. The measurement spot of the optical instrument is 140x when it measures grating stack 110x. The measurement spot then moves to 140y to measure grating stack 110y. Alternatively, the measurement instrument has two measurement spots 140x and 140y that perform spatially separated but simultaneous measurements. Grating stack 110x has a lower grating 120x and an upper grating 130x. Gratings 120x and 130x differ at least in one dimension. In FIG. 5, the upper grating 130x is shown to be shorter than grating 120x in the direction of the grating lines. The dimensions of the gratings are such that, both gratings 120x and 130x completely cover the measurement spot 140x. The same apply to grating stack 110y, lower grating 120y, upper grating 130y, and measurement spot 140y. The distances $x_1$, $x_2$, $y_1$, and $y_2$ shown in FIG. 5 are the widths of the strips where only one of the gratings is visible looking down on the wafer. The x-component of the gross overlay is obtained as $\Delta X=(x_1-x_2)/2$. Process induced errors that affect the distances $x_1$ and $x_2$ in the same manner are canceled by the differencing operation. In the alternative embodiment shown in FIG. 6, the lower and upper gratings differ in both dimensions. The distances $x_1$, $x_2$, $y_1$, and $y_2$ are measured on the image of one or more grating stacks.

Figure 7:
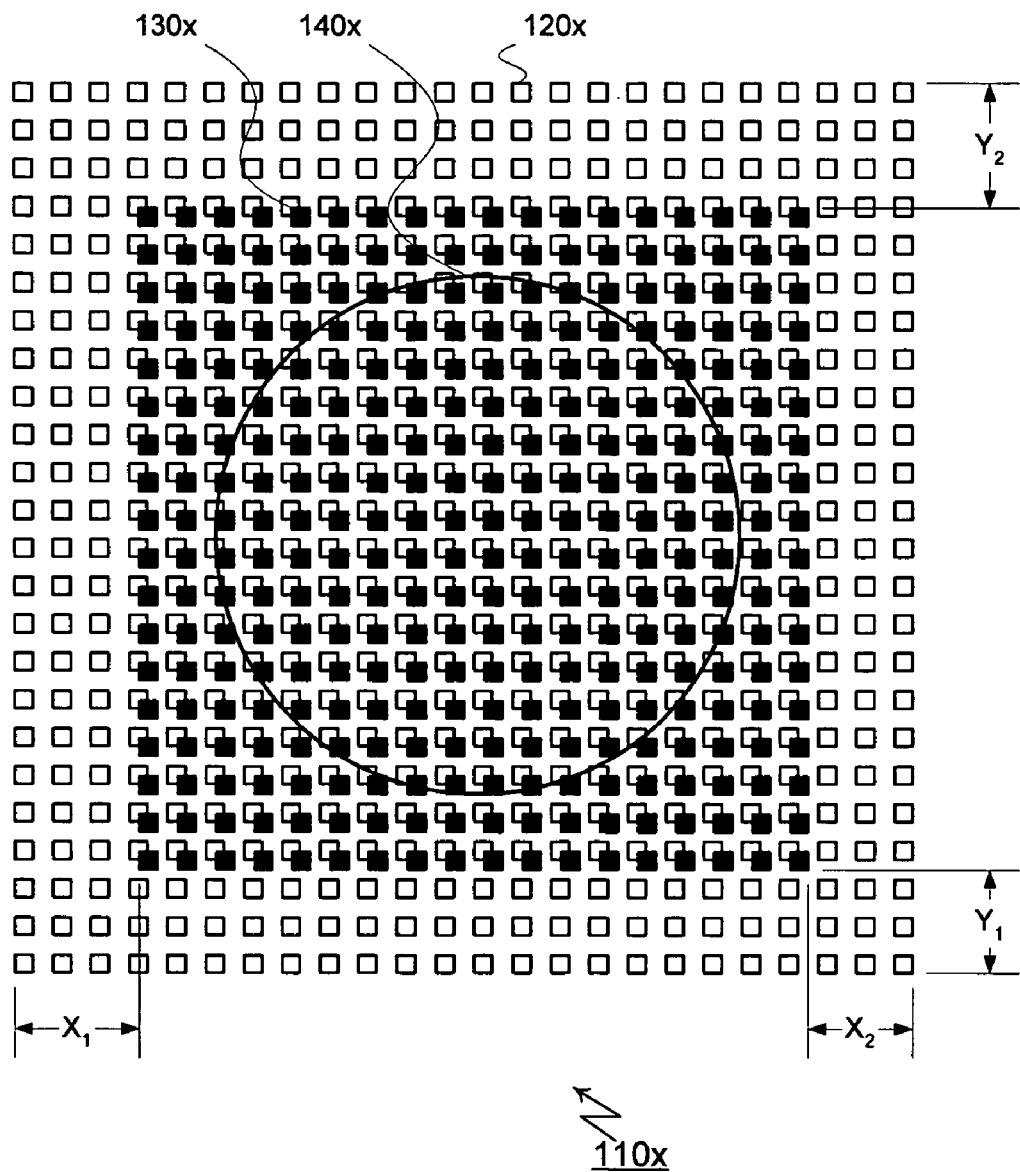
FIG. 7 shows another embodiment for the overlay metrology target configured, in this case using 2-dimensional arrays of three-dimensional features such as contact holes, posts, islands.
Figure 8:
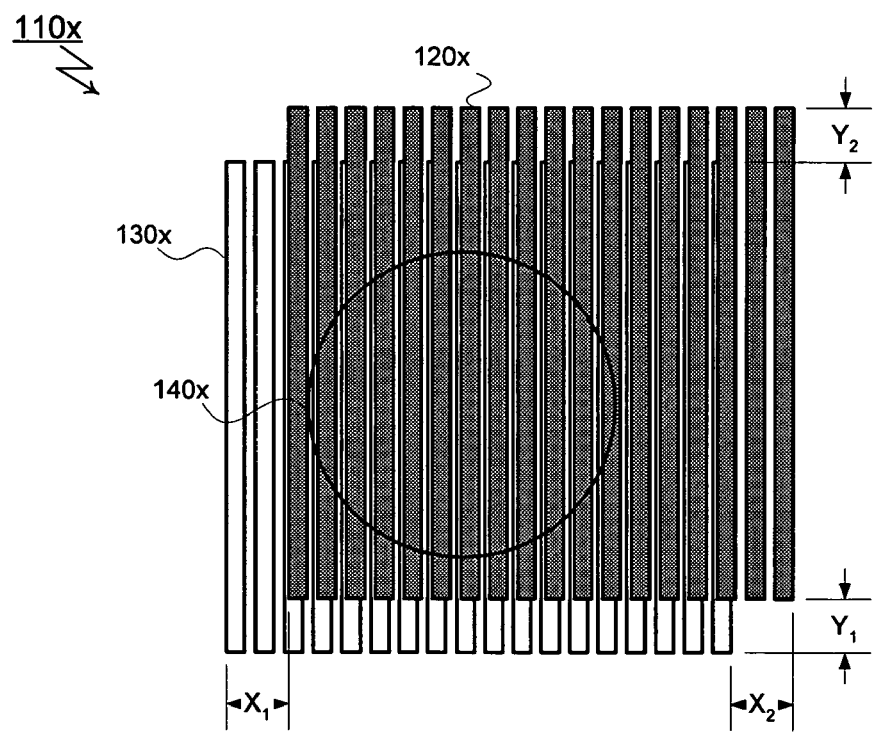
FIG. 8 shows another embodiment for the overlay metrology target configured, in this case to measure overlay in two directions using a single grating stack with each layer in the grating stack being the same size.

FIG. 7 shows an alternative embodiment where the lower and upper gratings are 2-dimensional arrays of features such as contact holes, posts, islands or other 3-dimensional features. The distances $x_1$, $x_2$, $y_1$, and $y_2$ are measured on the image of one or more grating stacks. FIG. 8 shows an alternative embodiment where the upper 130x and lower 120x gratings have the same dimensions. The lower and upper gratings are preferably printed with an offset bias that is large enough to be measured by the imaging system. The overlay is obtained as $\Delta X=(x_1+x_2)/2-$(offset bias). This embodiment is not preferred because gross overlay is not obtained from the difference of two similar distances.

Figure 9:
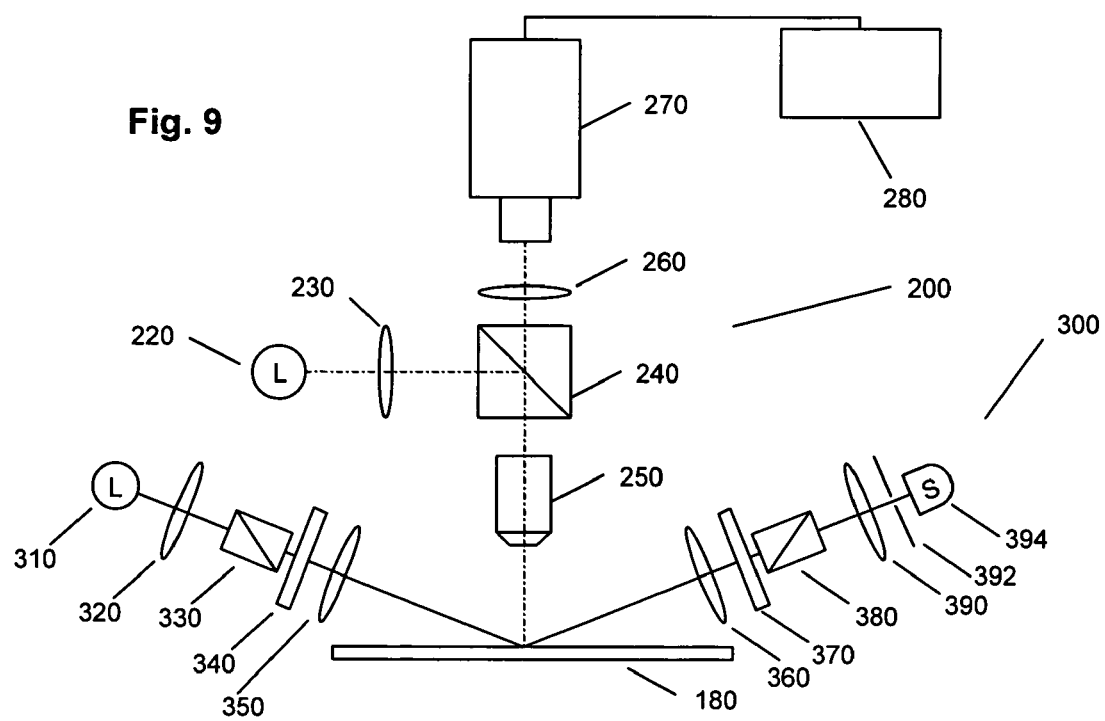
FIG. 9 shows a schematic diagram of a measurement instrument.

A vision system 200, such as the one shown in FIG. 9, is used to navigate and find the metrology targets on the wafer 180 and also to measure the distances $x_1$, $x_2$, $y_1$, and $y_2$. The vision system consists of a light source 220, condenser or illumination optics 230, beam splitter 240, objective 250, tube-lens 260, camera 270 with a CCD or CMOS array detector, image processor 280.

In the preferred implementation, the vision system 220 is separate from the system that measures the optical properties of the grating as a function of wavelength or angle of incidence or both. For example, FIG. 9 shows an oblique incidence ellipsometer 300 that measures the optical properties of the gratings. The components of ellipsometer 300 are broadband light source 310, collimator 320, rotary polarizer 330, optional rotary waveplate 340, refractive or reflective illumination objective 350, collection objective 360, optional rotary waveplate 370, rotary polarizer 380, re-imaging optics 390, pinhole 392, grating spectrometer 394. Optical components 230, 250, 260, 320, 350, 360, and 390 can be compound refractive or reflective lenses. A normal or oblique incidence, polarized or unpolarized reflectometer can also be used to measure the optical properties of the grating stacks. The spectroscopic metrology system can also share its optical path with the vision system (not shown in FIG. 9).

The vision system measures the distances $x_1$, $x_2$, $y_1$, $y_2$, and some known and well-controlled distance $G_x$, and $G_y$ to calibrate the pixels in micrometers. In the simplest example, $G_x$, and $G_y$ can be the x and y dimensions of a grating as shown in FIG. 5. This embodiment is not preferred because line end shortening would affect $G_y$. In a more preferred embodiment, the calibration distances $G_x$, and $G_y$ are distances between identical features. The following differences are formed from the measurements of the vision system:

$$\Delta X_{VISION}=(x_1-x_2)/2 \quad (5)$$

$$\Delta Y_{VISION}=(y_1-y_2)/2 \quad (6)$$

This is similar to the box-in-box measurements in imaging-based prior art except the boxes are not stacks of thin films but stacks of gratings. The overlay measurement ($\Delta X_{VISION}$, $\Delta Y_{VISION}$), which is a measurement of gross overlay, is less precise than grating measurements but it has a significantly larger measurement range. The range of the overlay measurement by the vision system is equal to the distance from the grating stack to the edge of the field of view of the camera or the distance from the grating stack to the nearest structure on the wafer, whichever distance is smaller. Typically, this range is at least 2 micrometers.

Embodiment-1 for Combining Image and Diffraction-based Overlay Measurements

In one embodiment of the invention, overlay is measured as:

$$\Delta x_{MEAS} = \begin{cases} \Delta x_{GRATING} & \text{if } |\Delta x_{VISION}| < \frac{P}{4} \\ \Delta x_{VISION} & \text{if } |\Delta x_{VISION}| \geq \frac{P}{4} \end{cases} \quad (7)$$

Figure 10:
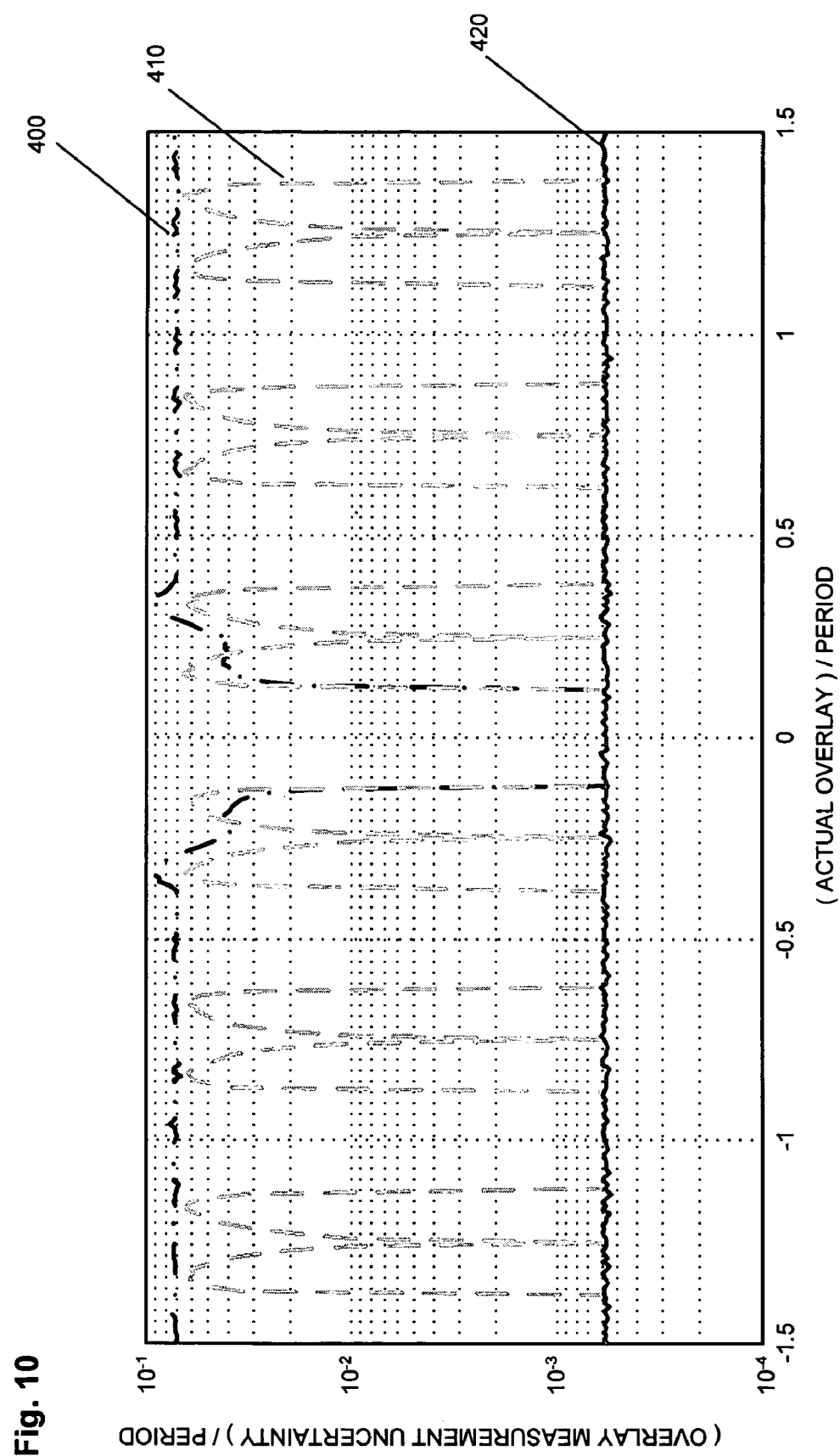
FIG. 10 shows the measurement uncertainties for three embodiments of the present invention as a function of actual overlay.

The total measurement uncertainty of the vision-based overlay measurement, $TMU_{VISION}$, is preferably no greater than P/8. The y-component of overlay is calculated in an analogous fashion. In this embodiment, the measurement uncertainty is determined by the diffraction-based measurement when $|\Delta x_{ACTUAL}|<P/4-TMU_{VISION}$. The measurement uncertainty is determined by the vision system when $|\Delta x_{ACTUAL}|>P/4+TMU_{VISION}$. Curve 400 in FIG. 10 shows a Monte-Carlo simulation of the measurement uncertainty for this embodiment. In this simulation, the measurement uncertainties of the vision and grating systems are ±P/8 and ±P/1000 respectively. Random measurement errors were uniformly distributed in a ±P/8 neighborhood for the vision-based measurement and a ±P/1000 neighborhood for the diffraction-based measurement.

Embodiment-2 for Combining Image and Diffraction-based Overlay Measurements

In another embodiment of the invention, the vision and diffraction-based overlay measurements are combined as follows:

$$M = int\left[\frac{\Delta x_{VISION}}{P/2}\right] \quad (8)$$

$$\Delta x_{MEAS} = (-1)^M \Delta x_{GRATING} + M P/2$$

Figure 1:
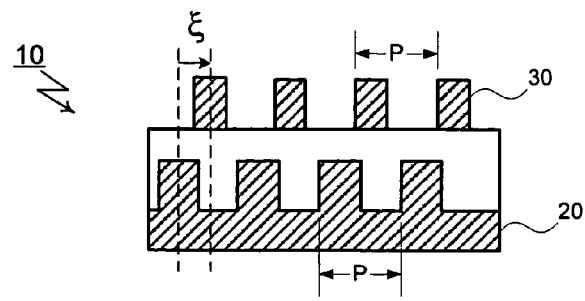
FIG. 1 shows in cross-section the stack of two gratings that are used in the diffraction-based overlay metrology in the prior art.
Figure 2:
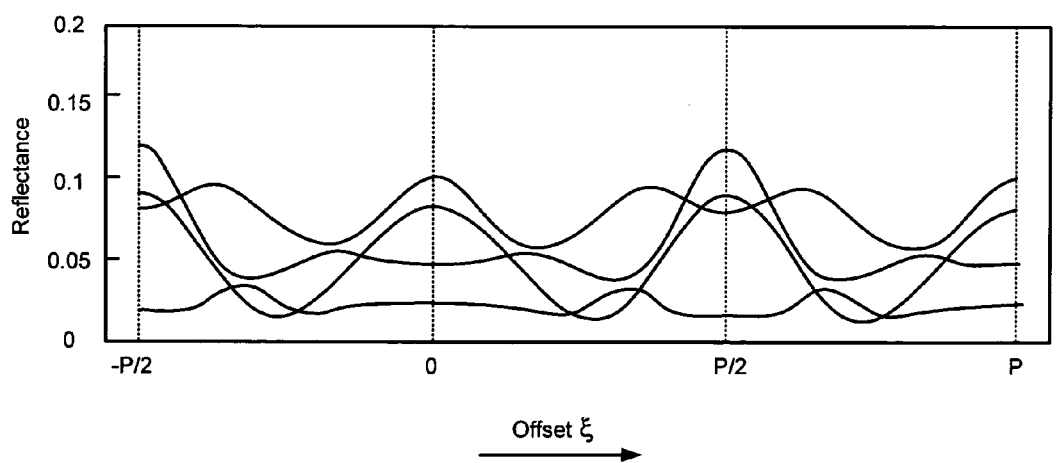
FIG. 2 shows calculated near-normal specular reflectance of the grating stack in FIG. 1 as a function of offset ξ for four different wavelengths.
Figure 3:
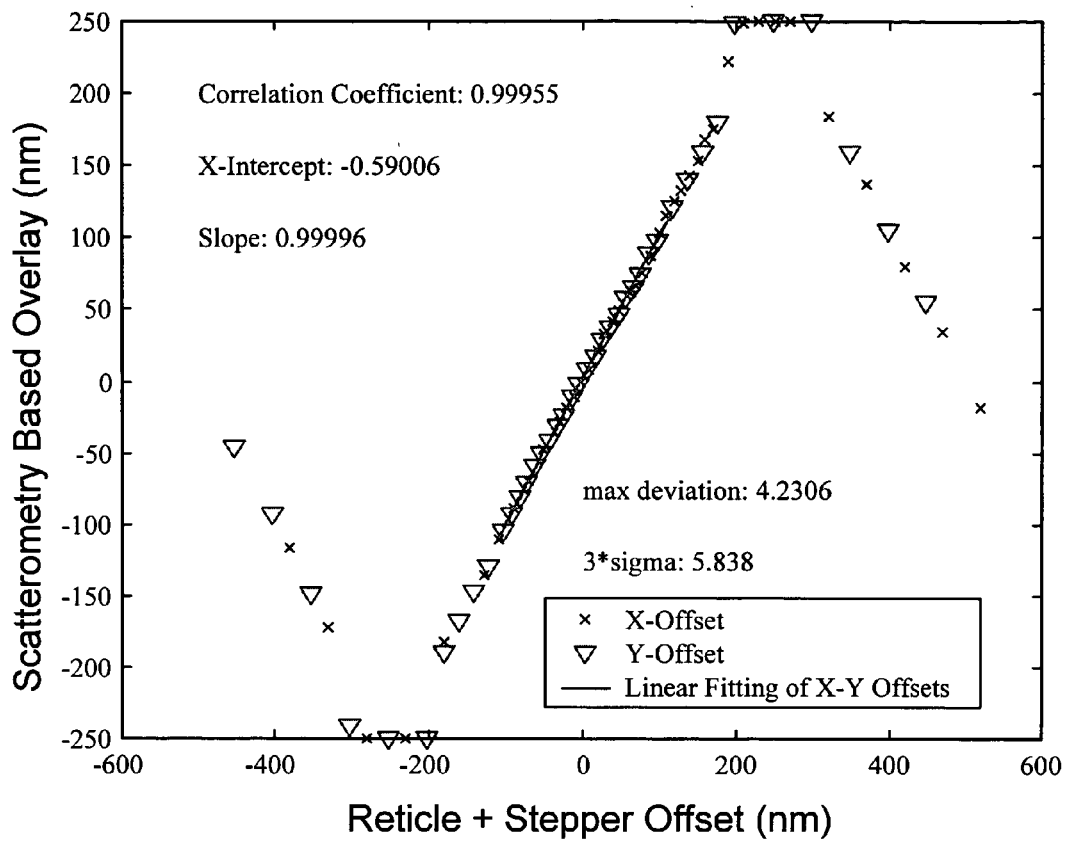
FIG. 3 shows the overlay measured using grating stacks as shown in FIG. 2 according to the prior art.
Figure 4:
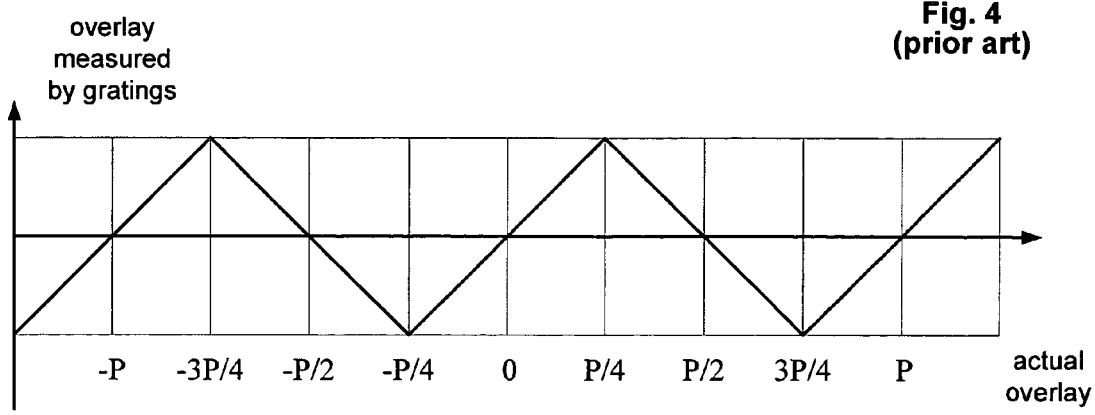
FIG. 4 is a graph that simplifies and illustrates the periodic nature of the graph in FIG. 3.

M is an estimate of the integer N in Equation (4). The estimate is obtained from the vision-based overlay measurement. Given that overlay is in $M^{th}$ half-period, a high-precision $\Delta x_{MEAS}$ is obtained from the diffraction-based measurement as described by the second equation in (8). The y-component of overlay is obtained in an analogous fashion. In this embodiment, the precision of overlay is determined by the diffraction-based measurement except at the dead-points of the diffraction-based measurement where the diffraction based-measurement is not sensitive to overlay. For a single grating stack with an offset bias of P/4, or for two grating stacks with offset biases of +P/4 and −P/4, sensitivity to overlay diminishes when overlay is an odd multiple of P/4 as seen in FIGS. 3 and 4. In this case, $\Delta x_{MEAS}$ according to Equation (8) has the precision of the diffraction based measurement for all overlay values except the ones close to odd multiples of P/4. When overlay is in a $TMU_{VISION}$ wide neighborhood of an odd multiple of P/4, the precision of $\Delta x_{MEAS}$ is equal to that of $\Delta X_{VISION}$. $TMU_{VISION}$ is required to be no larger than P/8 in this embodiment. The measurement uncertainty for this embodiment is shown by curve 410 in FIG. 10.

Embodiment-3 for Combining Image and Diffraction-based Overlay Measurements

In this embodiment, at least two grating stacks are used to measure overlay in one direction. The two gratings differ in offset bias by P/4. They yield the following diffraction-based overlay measurements, not accounting for measurement errors:

$$N_1 = int\left[\frac{\Delta x_{ACTUAL}}{P/2}\right] \quad (8)$$

$$\Delta x_{GRATING-1} = (-1)^{N_1}[\Delta x_{ACTUAL} - N_1 P/2]$$

$$N_2 = int\left[\frac{\Delta x_{ACTUAL} + (P/4)}{P/2}\right]$$

$$\Delta x_{GRATING-2} = (-1)^{N_2}[\Delta x_{ACTUAL} + (P/4) - N_2 P/2]$$

The overlay measurements are combined as follows:

$$M_1 = int\left[\frac{\Delta x_{VISION}}{P/2}\right] \quad (9)$$

$$M_2 = int\left[\frac{\Delta x_{VISION} + (P/4)}{P/2}\right]$$

$$\Delta x_{MEAS} = \begin{cases} \Delta x_{GRATING-1}(-1)^{M_1} + M_1(P/2) & \text{if } |\Delta x_{GRATING-1}| < P/8 \\ \Delta x_{GRATING-2}(-1)^{M_2} + M_2(P/2) - (P/4) & \text{if } |\Delta x_{GRATING-1}| \geq P/8 \end{cases}$$

Provided that $TMU_{VISION}$ is no greater than P/8, the precision of $\Delta x_{MEAS}$ is equal to the precision of the diffraction-based overlay even for gross overlay. The measurement uncertainty for this embodiment is shown by curve 420 in FIG. 10.

What is claimed is:

1. A method for optically inspecting and evaluating a sample fabricated with lithography process, the method comprising:
    projecting a probe beam at an overlay metrology target included in the sample, where the overlay metrology target includes one or more gratings built into an upper layer of the sample, each of which is paired with a respective grating built into a lower layer of the sample;
    analyzing the diffraction imparted to the probe beam by the gratings of the overlay target to measure fine overlay between the upper and lower layers;
    measuring the overlay metrology target by optical microscopy to determine the gross overlay between the upper layer and the lower layer of the sample;
    generating a total overlay measurement that is consistent with both the fine and gross overlay measurements; and
    using the total overlay measurement to control the lithography process.

2. A method as recited in claim 1 in which the gross overlay is measured using the images of one or more pairs of gratings.

3. A method as recited in claim 2 in which at least one grating-pair has gratings of different size in the upper and lower layers.

4. A method as recited in claim 1 in which gross overlay is measured using an imaging system that is used for navigation or pattern recognition to locate overlay metrology targets.

5. A method as recited in claim 1 in which the total overlay measurement equals the gross overlay if the gross overlay exceeds a threshold, and the total overlay measurement equals the fine overlay if the gross overlay is equal to or less than the threshold.

6. A method as recited in claim 1 in which the method further comprises the steps of:
    determining a range of unambiguous fine overlay measurements;
    determining from the gross overlay measurement the integer count of whole fine-measurements ranges nearest to the total overlay;
    forming a product by multiplying the integer count by the fine-measurement range; and
    adding or subtracting the fine overlay measurement to the product.

7. An overlay metrology target that comprises: one or more upper gratings formed on an upper layer of a sample, each grating having a plurality of repeating elements having a period, each paired with a respective lower grating formed on a lower layer of the sample, each grating having a total width dimension (X) and a total length dimension (Y), with at least one grating on the upper layer differing in at least one of the X or Y dimensions than its grating pair an amount sufficient to facilitate measurement of gross overlay by an optical microscope; said amount being greater than twice the period.

8. An overlay target as recited in claim 7 in which one grating is differently sized in the X dimension than its grating pair and one grating is differently sized in the Y dimension than its grating pair.

9. An overlay target as recited in claim 7 in which one grating is differently sized in the X and Y dimensions than its grating pair.

10. An overlay target as recited in claim 7 in which each grating is formed as a parallel series of lines.

11. An overlay target as recited in claim 10 in which the lines in the upper and lower grating of each pair are parallel to each other and at least one grating differs from its pair in the dimension that is parallel to the grating lines.

12. An overlay target as recited in claim 7 in which each grating is formed as a two dimensional array of three dimensional features.

13. A method for controlling overlay layers within semiconductor wafers created by a lithography process, the method comprising:
    forming an overlay metrology target included in a sample, where the overlay metrology target includes one or more gratings built into an upper layer of the sample, each of which is paired with a respective grating built into a lower layer of the sample;

measuring the overlay metrology target to determine gross overlay between the upper layer and the lower layer of the sample;

measuring the overlay metrology target to determine fine overlay between the upper layer and the lower layer of the sample;

generating a total overlay measurement that is consistent with both the fine and gross overlay measurements; and using the total overlay measurement to control the lithography process.

14. A method as recited in claim 13 in which at least one grating-pair has gratings of different size in the upper and lower layers.

15. A method as recited in claim 13 in which gross overlay is measured using an imaging system that is used for navigation or pattern recognition to locate overlay metrology targets.

16. A method as recited in claim 13 in which at least one grating on the upper layer differs in at least one dimension or shape than its grating pair.

17. A method as recited in claim 16 in which one grating is differently sized in the X dimension than its grating pair and one grating is differently sized in the Y dimension than its grating pair.

18. A method as recited in claim 16 in which one grating is differently sized in the X and Y dimensions than its grating pair.

19. A method as recited in claim 13 in which each grating is formed as a parallel series of lines.

20. A method as recited in claim 19 in which the lines in the upper and lower grating of each pair are parallel to each other and at least one grating differs from its pair in the dimension that is parallel to the grating lines.

21. A method as recited in claim 13 in which each grating is formed as a two dimensional array of three-dimensional features.

22. A method for monitoring overlay of layers in a semiconductor wafer created by a lithography process comprising the steps of:

forming an overlay metrology target included in a sample, where the overlay metrology target includes at least one pair of gratings, one grating of the pair being built into an upper layer of the sample and the other grating of the pair being built into a lower layer of the sample, with the grating in the upper layer differing in at least one dimension or shape from the grating in the lower layer;

measuring the gross overlay metrology target to determine overlay between the upper layer and the lower layer of the sample using optical microscopy;

measuring the fine overlay metrology target to determine overlay between the upper layer and the lower layer of the sample using a scatterometry approach;

generating a total overlay measurement that is consistent with both the fine and gross overlay measurements; and using the total overlay measurement to control the lithography process.

\* \* \* \* \*